United States Patent [19]

Stern

[11] Patent Number: 5,277,201
[45] Date of Patent: Jan. 11, 1994

[54] ENDOMETRIAL ABLATION APPARATUS AND METHOD

[75] Inventor: Roger A. Stern, Cupertino, Calif.

[73] Assignee: Vesta Medical, Inc., Palo Alto, Calif.

[21] Appl. No.: 877,567

[22] Filed: May 1, 1992

[51] Int. Cl.$^5$ .............................................. A61N 5/00
[52] U.S. Cl. ...................................... 607/98; 606/32; 606/41; 607/99; 607/138
[58] Field of Search ............... 606/32, 33, 40, 41, 606/45, 49, 27, 28; 128/784, 786, 788, 804, 401

[56] References Cited

U.S. PATENT DOCUMENTS

| | | |
|---|---|---|
| 1,827,306 | 10/1931 | Chapman et al. |
| 3,324,847 | 6/1967 | Zoumboulis |
| 3,369,549 | 2/1968 | Armao |
| 3,750,653 | 8/1973 | Simon |
| 3,789,829 | 2/1974 | Hasson |
| 3,840,016 | 10/1974 | Lindemann |
| 3,901,224 | 8/1975 | Bucalo |
| 3,924,628 | 12/1975 | Droegemueller et al. |
| 3,934,580 | 1/1976 | Cournut |
| 4,014,988 | 3/1977 | Pharriss et al. |
| 4,016,270 | 4/1977 | Pharriss et al. |
| 4,072,147 | 2/1978 | Hett |
| 4,102,342 | 7/1978 | Akiyama et al. |
| 4,160,455 | 7/1979 | Law |
| 4,198,981 | 4/1980 | Sinnreich |
| 4,292,960 | 10/1981 | Paglione |
| 4,296,760 | 10/1981 | Carlsson et al. |
| 4,311,154 | 1/1982 | Sterzer et al. |
| 4,349,033 | 9/1982 | Eden |
| 4,375,220 | 3/1983 | Matvias |
| 4,377,168 | 3/1983 | Rzasa et al. |
| 4,409,993 | 10/1983 | Furihata |

(List continued on next page.)

FOREIGN PATENT DOCUMENTS

| | | |
|---|---|---|
| 0115420 | 8/1984 | European Pat. Off. |
| 0407057A1 | 1/1991 | European Pat. Off. |
| 527331 | 9/1985 | Fed. Rep. of Germany |
| 3516830 | 11/1986 | Fed. Rep. of Germany ...... 128/786 |
| WO8701276 | 3/1987 | PCT Int'l Appl. |

OTHER PUBLICATIONS

"A Technique for Combining Microwave Hyperthermia With Intraluminal Brachytherapy of the Desophagus": M. A. Astrahan, et al.; Int. J. Hyperthermia, 1989, vol. 5, No. 1, pp. 37-51.

"Endometrial Ablation: An Alternative to Hysterectomy": May/Jun. 1991 The American Journal of Gynecologic Health, vol. V, No. 3; pp. 1-2.

"Microwave Applicator for BPH": M. A. Astrahan, et (List continued on next page.)

Primary Examiner—Lee S. Cohen
Attorney, Agent, or Firm—Oblon, Spivak, McClelland, Maier & Neustadt

[57] ABSTRACT

An endometrial ablation method comprising passing sufficient RF current having a frequency of from 250 kHz to about 100 MHz through substantially the entire surface of the endometrium to heat the endometrium, in a single operation, to a temperature within the range of from 45° C. to 90° C. and preferably not above 70° C. for a time sufficient to destroy the cells of the lining while maintaining the average temperature of the myometrium at a temperature below about 42° C. The apparatus comprises a electroconductive expandable member such as a balloon for extending the organ and effecting electrical contact with the endometrial lining to be destroyed. The balloon is connected to a power source adapted to provide radiofrequency electric power having the desired characteristics to selectively heat the endometrial lining to the desired temperature. The balloon can be an electroconductive elastomer such as a mixture of a polymeric elastomer and electroconductive particles. Alternatively, it can be a non-extensible bladder having a shape and size, in its fully expanded form, which will extend the organ and effecting contact with the endometrial lining to be destroyed. One surface of the non-extensible bladder can be coated with electroconductive material. The coating can be applied to the inner surface of the non-extensible bladder if the bladder wall thickness is less than about 25 mm.

15 Claims, 3 Drawing Sheets

U.S. PATENT DOCUMENTS

| | | |
|---|---|---|
| 4,469,103 | 9/1984 | Barrett . |
| 4,491,131 | 1/1985 | Vassiliadis . |
| 4,494,539 | 1/1985 | Zenitani et al. . |
| 4,549,533 | 10/1985 | Cain et al. . |
| 4,552,127 | 11/1985 | Schiff . |
| 4,572,190 | 2/1986 | Azam et al. . |
| 4,622,972 | 11/1986 | Giebeler, Jr. . |
| 4,638,436 | 1/1987 | Badger et al. . |
| 4,658,836 | 4/1987 | Turner . |
| 4,662,383 | 5/1987 | Sogawa et al. . |
| 4,674,481 | 6/1987 | Boddie, Jr. et al. . |
| 4,676,258 | 6/1987 | Inokuchi et al. . |
| 4,692,452 | 9/1987 | Cerny et al. . |
| 4,700,701 | 10/1987 | Montaldi . |
| 4,754,752 | 7/1988 | Ginsburg et al. . |
| 4,754,757 | 7/1988 | Feucht . |
| 4,758,592 | 7/1988 | Horrobin et al. . |
| 4,771,778 | 9/1988 | Mar . |
| 4,773,899 | 9/1988 | Spears . |
| 4,776,349 | 10/1988 | Nashef et al. . |
| 4,818,954 | 4/1989 | Flachenecker et al. . |
| 4,823,812 | 4/1989 | Eshel et al. . |
| 4,836,189 | 6/1989 | Allred, III et al. . |
| 4,852,579 | 8/1989 | Gilstad et al. . |
| 4,860,752 | 8/1989 | Turner . |
| 4,865,047 | 9/1989 | Chou et al. . |
| 4,927,413 | 5/1990 | Hess . |
| 4,935,003 | 6/1990 | Gainutdinova et al. . |
| 4,938,217 | 7/1990 | Lele . |
| 4,946,440 | 8/1990 | Hall . |
| 4,949,718 | 8/1990 | Neuwirth et al. . |
| 4,955,377 | 9/1990 | Lennox et al. . |
| 4,960,109 | 10/1990 | Lele . |
| 4,961,435 | 10/1990 | Kitagawa et al. . |
| 4,967,765 | 11/1990 | Turner et al. . |
| 4,974,587 | 12/1990 | Turner et al. . |
| 4,979,948 | 12/1990 | Gedded et al. . |
| 4,985,027 | 1/1991 | Dressel . |
| 4,993,430 | 2/1991 | Shimoyama et al. . |
| 4,997,653 | 3/1991 | Igarashi . |
| 4,998,930 | 3/1991 | Lundahl . |
| 5,003,991 | 4/1991 | Takayama et al. . |
| 5,006,119 | 4/1991 | Acker et al. . |
| 5,026,959 | 6/1991 | Ito et al. . |
| 5,032,124 | 7/1991 | Menton . |
| 5,035,694 | 7/1991 | Kasprzyk et al. ............... 606/27 |
| 5,041,089 | 8/1991 | Mueller et al. . |
| 5,045,056 | 9/1991 | Behl . |
| 5,050,597 | 9/1991 | Daikuzono . |
| 5,057,106 | 10/1991 | Kasevich et al. ............... 128/786 X |
| 5,059,191 | 10/1991 | Beyer et al. . |
| 5,084,044 | 1/1992 | Quint . |
| 5,092,841 | 3/1992 | Spears . |
| 5,098,429 | 3/1992 | Sterzer . |
| 5,100,388 | 3/1992 | Behl et al. . |
| 5,188,122 | 2/1993 | Phipps et al. ............... 128/788 |

OTHER PUBLICATIONS al; Int. J. Hyperthermia, 1989, vol. 5, No. 3, pp. 283–296.

"New Concepts in Hysteroscopy": (Symposium) Contemporary OB/GYN; Jun. 1991, pp. 84–86, 89–90, 92, 94–97, 100 and 103.

"New Techniques in Operative Hysteroscopy": 1990 Audio-Digest Foundation; Side A-Side B, 3 pages.

Audio-Digest Obstetrics/Gynecology, vol. 37, No. 10, May 15, 1990.

"Resectoscopes for the Gynecologist": Philip G. Brooks, MD; Contemporary OB/GYN; pp. 51–52 and 56–57; Dates Unknown.

"Treatment of Functional Menorrhagia by Radio-frequency-Induced Thermal Endometrial Ablation": J. H. Phipps, et al; The Lancet 1990 (Feb. 17, 1990); vol. 335, pp. 374–376.

"Treatment of Menorrhagia by Radiofrequency Heating": M. V. Prior, et al; Int. J. Hyperthermia, 1991, vol. 7, No. 2, pp. 213–220.

"Uterine Resectoscopes for Endometrial Ablation and Resection": Karl Storz; Karl Storz Endoscopy Advertisement; 2 pages, date unknown.

"Endometrial Ablation": Siegler, et al: Date Unknown, pp. 148–163.

Therapeutic Hysteroscopy: Indications and Techniques; Chapter 9 One (1) page from Article in TRENDS; 1991, Faulkner and Gray.

"Devices: Replacing the Roto-Rooter Invited Lectures": Dates Unknown; p. 24 with attached pp. 66 and 67, and 25.

ENDOMETRIAL ABLATION APPARATUS AND METHOD

FIELD OF THE INVENTION

This invention relates to a method and apparatus for the destruction of the inner lining of body organs. In one aspect, this invention relates to a method and apparatus for the selective destruction of the endometrium, an alternative to hysterectomy for treating uterine bleeding.

BACKGROUND OF THE INVENTION

Destruction of the inner lining of body organs provides an alternative to removal of the body organs for treating diseases and abnormal conditions. Techniques applied to this procedure have included destructive treatment of the inner linings with chemicals and with various forms of thermal energy such as radiofrequency and microwave heating, cryotherapy, laser and electrosurgery. Radiofrequency and microwave energies have also been applied directly to the linings to generate heat in situ. However, the procedures developed to date involve manual application of a small treatment tool to successive areas of the lining. This is an expensive operating room procedure, limiting its availability only to most severe conditions of amenorrhea, for example.

DESCRIPTION OF THE PRIOR ART

U.S. Pat. No. 4,979,948 describes thermal ablation of the mucosal layer of a gallbladder by resistive heating with an RF balloon electrode. Electric current is delivered from the balloon from a conductive expansion liquid filling the balloon. In contrast to the conductive balloon electrodes of this invention, this monopolar device has power loss in the conductive fluid and cannot be adapted to provide multiple electrodes, each with individual power control and/or a temperature sensor.

Balloon catheters supplied with a heated fluid have been used for thermal ablation of hollow body organs, as described in U.S. Pat. No. 5,045,056. Application of microwave and high frequency RF energy to body areas to destroy body tissue, using single electrodes enclosed in expanded balloons have been described in U.S. Pat. Nos. 4,662,383 and 4,676,258, for example.

OBJECTS AND SUMMARY OF THE INVENTION

It is an object of this invention to provide a method for endometrial ablation which is safe, rapid and can be carried out without maintaining visual contact with the endometrial lining being ablated.

It is another object of this invention to provide an apparatus and method for endometrial ablation which, for some conditions, can be carried out in a doctor's office on an out-patient basis, without requiring the use of an operating room.

In summary, the method of this invention for endometrial ablation comprises passing an amount of RF current having a frequency of at least about 250 kHz, preferably from 250 kHz to 100 MHz, from an expandable member conforming to the inner surface of the endometrium and filled with an electrically non-conductive medium. The RF current is passed through substantially the entire surface of the endometrium in an amount which is sufficient to resistively heat the endometrium in a single operation to a temperature within the range of from 45° C. to 90° C. for a time sufficient to destroy the cells of the lining while maintaining the average temperature of the myometrium at a temperature below about 42° C. The method can be carried out by inserting a conductive, expandable member in its unexpanded state into the uterine cavity through the cervical os, expanding the member to establish surface contact with the endometrial surface, and applying the RF current to the endometrium.

In summary, one embodiment of the endometrial ablation apparatus of this invention for selectively destroying the endometrial lining of a body organ comprises a electroconductive, expandable means such as a balloon for extending the organ and effecting electrical contact with the endometrial lining to be destroyed, the balloon being filled with an electrically non-conductive medium. The electroconductive expandable means is connected to a power source adapted to provide RF current having a frequency of at least about 250 kHz, preferably from 250 kHz to 100 MHz in an amount which is sufficient to resistively heat the endometrium in a single operation to a temperature within the range of from 45° C. to 90° C. for a time sufficient to destroy the cells of the lining while maintaining the average temperature of the myometrium at a temperature below about 42° C. When the expandable means is a fluid filled balloon, it is connected to a fluid source.

The electroconductive expandable means can comprise an electroconductive elastomer such as a mixture of a polymeric elastomer and electroconductive particles. Alternatively, it can be a non-extensible expandable composition having a shape and size, in its fully expanded form, which will distend the organ and effecting contact with the endometrial lining to be destroyed. One surface, either inner or outer surface, of the non-extensible means can be coated with electroconductive material. The coating can be applied to the inner surface of the expandable, non-extensible means provided the wall thickness thereof is sufficiently small to permit low impedance capacitive coupling of the RF energy to the tissue, preferably having a thickness of less than about 0.3 mm and optimally from 0.05 to 0.25 mm.

DETAILED DESCRIPTION OF THE INVENTION

In general the apparatus of this invention is an monopolar electrode system which expands to conform to the endometrial surface to be treated, dilating and stretching the endometrium to reduce surface folds. It passes radiofrequency electric current through the dilated endometrial surface for a time sufficient to destroy the endometrial cells, that is, to elevate the temperature of the endometrium to a temperature of from 45° C. to 90° C., preferably within 10 seconds and maintaining this temperature until the endometrial tissue is destroyed. Optimally, the temperature of the heating is from 55° C. to 65° C. for up to 10 minutes.

The electrical current is passed through or along the surface of the expandable member, the interior of the expandable member being filled with an electrically non-conductive substance such as a fluid. The expandable member can be any material or article which can be compressed or otherwise prepared in a small diameter configuration for insertion through the cervical os and expanded or inflated after the insertion to provide the dilation. It must be capable of establishing direct electrical connection or capacitive coupling with the endometrium. The other electrical contact is one or more conventional grounding plates or patches which contact a large area of the patient's skin to complete the circuit.

The electric current flowing through the tissue causes resistive heating due to conductance of the tissue. The power density diminishes with distance from the electrode as a reciprocal of the fourth power of the distance. Thus the heat generation is focused in the endometrium and the immediately surrounding muscular tissue, for example, the portion of the myometrium in contact with the lining. Since the myometrium is highly vascularized, heat removal from it is rapid. Consequently, the temperature of the endometrium can be heated to a destructive temperature faster than the remainder of the organ. With this controlled system, endometrial ablation can be safely accomplished as a simple medical procedure, using local anesthesia. It can be made more readily available at a fraction of the cost and with less hazard than the endometrial ablations known prior to this invention.

This invention is described hereinafter using balloons and/or bladders with a single inner fluid chamber as the expandable member for purposes of clarity of presentation. However, the expandable member can be any composition or material with one or more open or closed cells or chambers, which can be compressed or configured in a small diameter for insertion and which will expand or be expanded after insertion to establish the desired electrical contact with the full surface of the endometrium. These other materials are intended to be fully within the scope of electroconductive expandable member of the apparatus and method of this invention.

Figure 1:
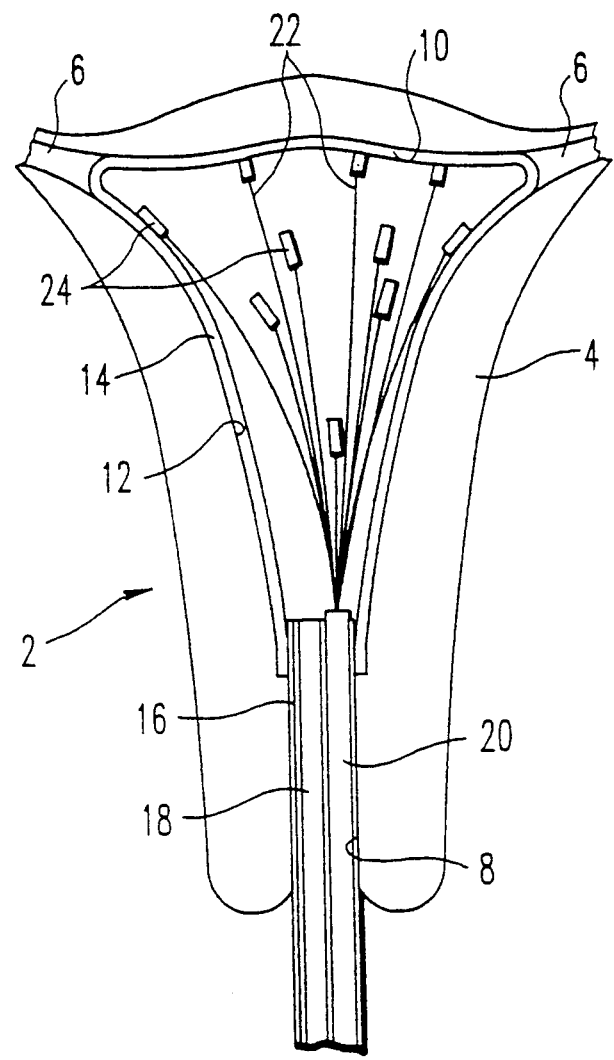
FIG. 1 is a schematic cross-sectional representation of an apparatus of this invention using an electroconductive balloon as the expandable member.
Figure 2:
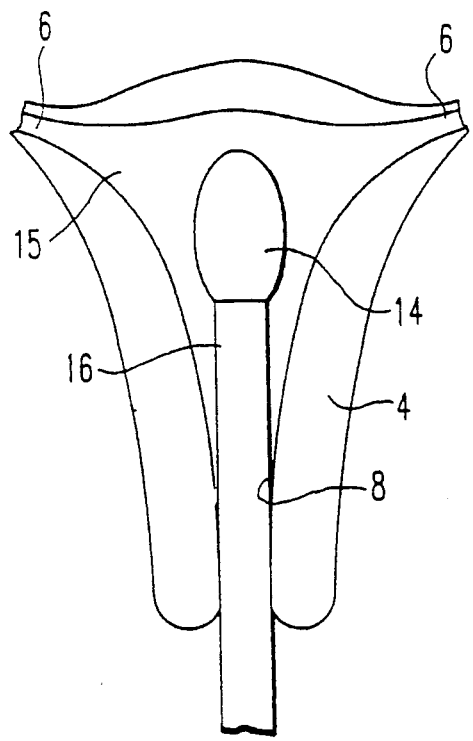
FIG. 2 is a schematic representation of the apparatus of FIG. 1, before inflation of the balloon element.

FIG. 1 is a schematic cross-sectional representation of an apparatus of this invention using an electroconductive balloon as the expandable member, and FIG. 2 is a schematic representation of the apparatus of FIG. 1, before inflation of the balloon element. The uterus 2 is composed of myometrial tissue 4 surrounding the uterine cavity. The normal uterine cavity or envelope is a flat cavity having approximately the shape of an inverted triangle, the two upper corners communicating with the ovaries by way of the fallopian tubes 6 and the bottom corner opening into the cervical canal or os 8. The entire surface of this envelope including the entrance to the fallopian tubes 6 and the cervical canal 8 is covered with a thin layer of tissue known as the uterine endometrium 12. The apparatus and method of this invention provide an improvement in the method of selective destruction of the endometrial cells.

The method of this invention comprises inserting an electroconductive expandable body such as an inflatable balloon or bladder into the uterine cavity 15 (FIG. 2) and subsequently inflating the balloon with fluid (gas or electrically non-conductive liquid) so that it extends the uterine cavity and conforms to the expanded surface thereof, as shown in FIG. 1. Portions of the balloon 14 extend into the entrance to the fallopian tubes 6 and extend along the entire endometrial surface 12 to the cervical os 8. The balloon is attached to and forms a fluid-tight seal with the tube 16. Tube 16 encloses a smaller fluid delivery tube 18 and electrical cable 20 containing a single common lead and additional sensor leads, an additional sensor lead being connected to each of a plurality of temperature sensors 24 attached to the inner surface of the balloon. Alternatively, this lead configuration can be replaced by lead pairs 22 for each sensor. The temperature sensors 24 are conventional thermistors or thermocouples and are positioned on zones of the balloon which will contact areas of the endometrial surface with are most sensitive to overheating. Alternatively, the temperature sensors can be fiber optic temperature sensors. The fluid delivery tube 18 is connected to a source of gas or liquid through a conventional fluid control system (not shown).

Figure 3:
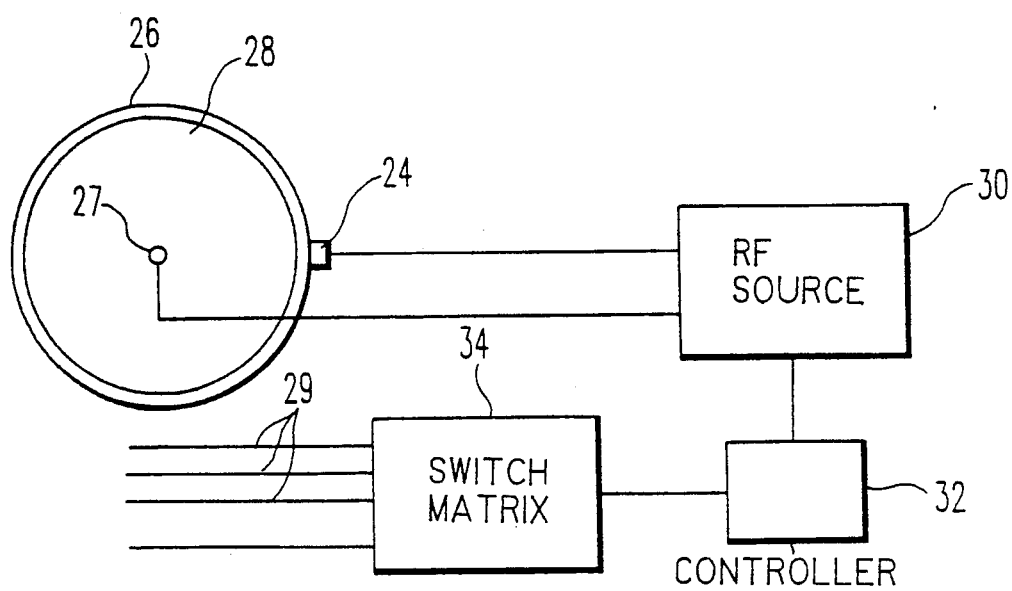
FIG. 3 is a schematic representation of the power source for the apparatus of FIG. 1.

FIG. 3 is a schematic representation of the power source for the apparatus of FIG. 1. The power source is adapted to provide radiofrequency electric power at a substantially constant amplitude to two electrodes at a frequency which, when current is passed from the balloon through the endometrial lining, will selectively heat the endometrial lining to a temperature within the range of from about 45° C. to about 90° C. and preferably not above 70° C. One electrode 27 is the electroconductive balloon 14 and the other electrode is an external electrode means 26 adapted to contact the outer surface of the body. The conductive balloon 14 forms one electrode 27 of a monopolar radiofrequency (RF) ablation device, the second or indifferent electrode 26 being located external to the body in the form of large surface area patches or plate electrodes. The tissue 28 between the electrodes is exposed and heated by the RF field and current flow created by the electrodes. The temperature sensor 24 and electrodes 26 and 28 are connected to a conventional, controllable RF source 30 and controller 32 such as a signal generator coupled with a power amplifier and a computer controller. The signal generator, power amplifier and computer controller are conventional and non-critical devices in the art. If the temperature sensor is a fiber optic device, it is coupled to the RF source and controller through a suitable conventional interface (not shown) which can convert the optical signal to data readable by the computer controller.

The leads leading to the temperature sensors 24 are connected to the input terminals of switch matrix 34 which can close the circuit with each of the temperature sensors sequentially and/or selectively. If any temperature sensor sampling indicates that a threshold temperature has been exceeded, the controller 32 can reduce or terminate power delivered to the balloon by &he RF source 30.

Figure 4:
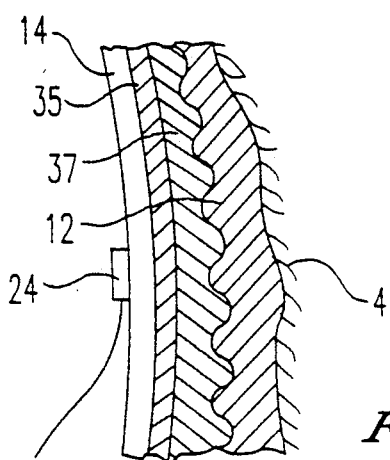
FIG. 4 is a schematic, enlarged cross-section of a the relationship between a small segment of uterine endometrium and the expandable element of this invention.

FIG. 4 is a schematic, enlarged cross-section of a the relationship between a small segment of uterine endometrium and the expandable balloon element of this invention. The endometrial lining 12, supported on the myometrium 4, is usually an irregular surface, even after being extended. The electrical contact between the conductive surface 35 on the outer surface of balloon 14 and the endometrium 12 can be improved by covering the outer surface of the balloon with a conventional electroconductive solution, paste or gel 37 which is physiologically non-toxic and non-irritating. Suitable electroconductive media include the known types of gels and pastes used as surface coatings for defibrillators, for example. Examples of suitable conductive gels are carboxymethylcellulose gels made from aqueous electrolyte solutions such as physiological saline solutions and the like. The electroconductive solution, paste or gel enhances electrical contact between the balloon and the endometrium by filling the pores of the balloon surface and the irregularities in the endometrial surface.

The expandable balloon or bladder can be an elastomeric polymer such as a natural or synthetic rubber made conductive by mixing the polymer with electroconductive particles such as carbon or conductive metal particles. Alternatively, it can be made conductive by a surface coating of electroconductive material such as an electroconductive gel, or a conductive metal coating on the outer or inner surface of the balloon or bladder wall. Electroconductive coatings can be applied to organic polymer surfaces by conventional vapor deposition, electrical deposition, sputtering and the like.

A preferred balloon comprises a thin, non-extensible polymer film such as a polyester (MYLAR) or other flexible thermoplastic or thermosetting polymer film, for example, having a conductive metal coating on the outer or inner surface thereof. The film forms a non-extensible bladder having a shape and size, in its fully expanded form, which will extend the organ and effecting contact with the endometrial lining to be destroyed. The inner surface of the non-extensible bladder can be coated with electroconductive material provided that the bladder wall thickness is less than about 0.25 mm.

The surface of the expandable member can be open-cell, porous material such as a foam or similar caged network of material which can hold the quantity of the electroconductive solution, paste or gel required to secure good electrical contact with the opposed endometrial surface. The surface can be coated with or impregnated with the electroconductive substance.

Figure 5:
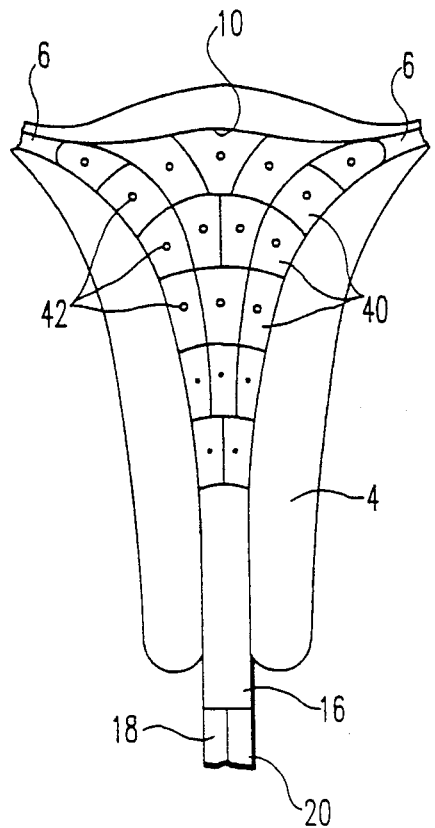
FIG. 5 is a schematic representation of an apparatus of this invention using a balloon as the expandable member, the balloon having a plurality of surface segments, each with a separate conductive surface and a temperature sensor.

FIG. 5 is a schematic representation of an apparatus of this invention using a balloon with a plurality of surface segments as the expandable member, each with a conductive surface and a temperature sensor. In this embodiment the balloon or inextensible bladder has a segmented electrode coating of electroconductive metal on either the inner or the outer surface thereof to permit controlled delivery of power to each segment. Each conductive segment 40 is electrically connected through conventional leads (not shown) to the power source. Each conductive segment 40 also has a temperature sensor 42 which is connected through conventional leads (not shown) to the switch matrix.

The segmented embodiment shown in FIG. 5 can be used in a monopolar or bipolar mode.

Figure 6:
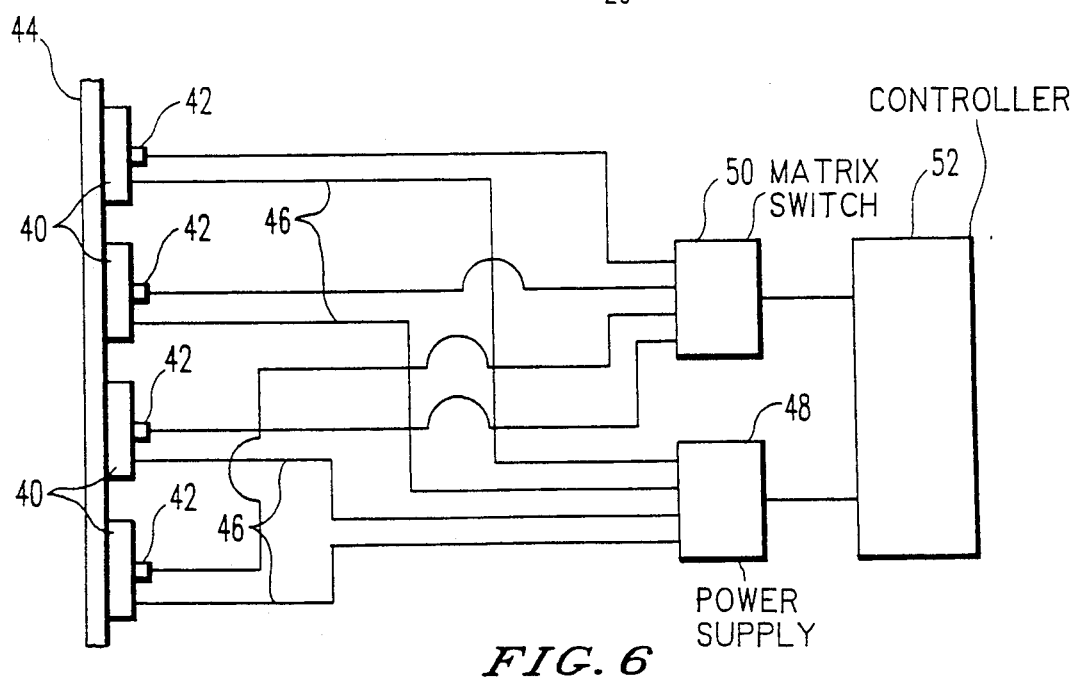
FIG. 6 is a schematic representation of the power source for the multi-segmented balloon shown in FIG. 5.

FIG. 6 is a schematic representation of the power source and switch matrix for the multi-segmented balloon shown in FIG. 5. The surface of the bladder 44 has attached thereto the conductive electrode segments 40 and the temperature sensors 42. Electrical leads 46 separately connect each electrode segment 40 to the power supply 48. Electrical leads 48 separately connect each temperature sensor 42 to the matrix switch 50. In response to the matrix switch, each temperature sensor is sampled, and the signal therefrom is fed to the controller. In response to the controller 52, power is applied to each conductive segment as required to maintain the temperature of the corresponding endometrium segment within the desired range during the treatment. It will be readily apparent to a person skilled in the art that the power can be applied simultaneously, sequentially or any other desired pattern to the electrode segments.

The invention claimed is:

1. An ablation method for treating an endometrium surrounded by a myometrium and having an inner surface comprising passing sufficient RF current, having a frequency of at least about 250 kHz, from an expandable member conforming to the inner surface of the endometrium and filled with an electrically non-conductive medium, through the inner surface of the endometrium to resistively heat substantially, the entire endometrium, in a single procedure, to a temperature within the range of from 45° C. to 90° C. for a time sufficient to destroy the cells of the endometrium while maintaining the average temperature of the myometrium at a temperature below about 42° C.

2. An endometrial ablation method of claim 1 wherein the temperature of the surface of the endometrium being heated is monitored and RF current through the endometrium is reduced in the event a selected temperature threshold is exceeded.

3. An endometrial ablation apparatus for selectively destroying the endometrial lining of an organ in a body having an outer surface comprising an electroconductive, expandable electrode means for extending the organ and effecting electrical contact with the endometrial lining to be destroyed and an external electrode means adapted to contact the outer surface of the body; the expandable electrode means containing an electrically non-conductive expansion medium; and a power source connected to the expandable electrode means and to the external electrode means, the power source being adapted to provide radio-frequency electric power to the expandable electrode means at a frequency of at least about 250 kHz in an amount which, when current is passed from the expandable electrode means through the endometrial lining, will selectively heat the endometrial lining to a temperature within the range of from about 45° C. to 90° C.

4. An endometrial ablation apparatus of claim 3 wherein the frequency is within the range of from about 250 kHz to about 100 MHz.

5. An endometrial ablation apparatus of claim 3 wherein the expandable electrode means is an electroconductive balloon adapted to be connected to an expansion fluid inlet means, the balloon being filled with an gas or an electrically non-conductive liquid.

6. An endometrial ablation apparatus of claim 5 wherein the balloon comprises an electroconductive, elastomer.

7. An endometrial ablation apparatus of claim 6 wherein the elastomer is a mixture of a polymeric elastomer and electroconductive particles.

8. An endometrial ablation apparatus of claim 3 wherein the expandable electrode means is a non-extensible bladder having a shape and size, in its fully expanded form, which will extend the organ and effecting contact with the endometrial lining to be destroyed.

9. An endometrial ablation apparatus of claim 8 wherein at least one surface of the non-extensible bladder is coated with electroconductive material.

10. An endometrial ablation apparatus of claim 9 wherein the non-extensible bladder has an inner surface which is coated with electroconductive material and the bladder wall thickness is less than about 0.25 mm.

11. An endometrial ablation apparatus of claim 3 wherein the expandable electrode means has an outer surface which is coated with electroconductive material.

12. An endometrial ablation apparatus of claim 11 wherein the expandable electrode means is an expandable balloon coated with an electroconductive metal coating.

13. An endometrial ablation apparatus of claim 11 wherein the outer surface of the expandable electrode means is coated or impregnated with an electroconductive liquid, paste or gel.

14. An endometrial ablation apparatus of claim 3 wherein the expandable electrode means has a surface to which at least one temperature sensor is connected.

15. An endometrial ablation apparatus of claim 14 including a control means connected to the power source and to the expandable electrode means, the control means being a means for reducing the power output from the power source to the expandable electrode means, wherein the temperature sensor is connected to the control means.

* * * * *